(12) United States Patent
Sipos

(10) Patent No.: US 8,735,377 B1
(45) Date of Patent: May 27, 2014

(54) METHODS OF TREATING HERPES ZOSTER

(76) Inventor: Susan Anna Sipos, Forest Hills, NY (US)

( * ) Notice: Subject to any disclaimer, the term of this patent is extended or adjusted under 35 U.S.C. 154(b) by 319 days.

(21) Appl. No.: 12/931,554

(22) Filed: Feb. 4, 2011

Related U.S. Application Data

(60) Provisional application No. 61/301,455, filed on Feb. 4, 2010.

(51) Int. Cl.
*A01N 37/18* (2006.01)
*A61K 31/65* (2006.01)

(52) U.S. Cl.
USPC .......................................................... 514/152

(58) Field of Classification Search
USPC .......................................................... 514/152
See application file for complete search history.

(56) References Cited

U.S. PATENT DOCUMENTS 7,223,416 B2 * 5/2007 Peyman ........................ 424/434

* cited by examiner

*Primary Examiner* — Yong Chong
(74) *Attorney, Agent, or Firm* — Susan A. Sipos

(57) ABSTRACT

A method of treating shingles in a human in need thereof. The method comprises administering a tetracycline compound in an amount that is effective to treat shingles, but has substantially no antibacterial activity.

15 Claims, No Drawings

METHODS OF TREATING HERPES ZOSTER

This application claims the benefit of U.S. Provisional Application No. 61/301,455, filed Feb. 4, 2010, which is incorporated herein by reference in its entirety.

BACKGROUND OF THE INVENTION

Herpes zoster (or simply zoster), commonly known as shingles and also known as zona, is a viral disease characterized by painful skin lesions (typically, a blistering rash) in a limited area on one side of the body. Shingles is caused by the varicella zoster virus (VZV).

Initial infection with VZV causes the short-lived illness chickenpox, and generally occurs in children. Once an episode of chickenpox has resolved, the virus is not eliminated from the body. Varicella zoster virus becomes latent in the nerve cell bodies and, less frequently, in non-neuronal satellite cells of dorsal root, cranial nerve or autonomic ganglion, without causing any symptoms. Years or decades after a chickenpox infection, the virus may reactivate as shingles. The virus breaks out of nerve cell bodies and travels down nerve axons to cause viral infection of the skin in the region of the nerve (i.e., the dermatome) causing painful skin lesions. Exactly how the virus remains latent in the body, and subsequently reactivates is not understood.

Throughout the world, the annual incidence rate of shingles ranges from 1.2 to 3.4 cases per 1,000 healthy individuals, increasing to 3.9-11.8 per 1,000 individuals older than age 65. Shingles develops in an estimated 500,000 Americans each year.

The earliest symptoms of shingles typically include headache, fever and malaise. These symptoms are commonly followed by sensations of burning pain, itching, hyperesthesia (i.e., oversensitivity), or paresthesia (i.e., tingling, pricking, numbness). Sensations are also described as stinging, aching and/or throbbing, and intermittent quick stabs of agonizing pain.

In most cases, after 1-2 days (but sometimes as long as 3 weeks), the initial phase is followed by the appearance of the characteristic painful skin lesions. The lesions most commonly occur on the torso, but can also appear on the face, eyes or other parts of the body. Shingles causes skin changes limited to a dermatome, normally resulting in a stripe or belt-like pattern that is limited to one side of the body and does not cross the midline.

Later, the lesions become vesicular, forming small blisters filled with a serous exudate, as the fever and general malaise continue. These lesions are typically described as being intensely painful. Since nerves carry the virus and the virus causes inflammation, shingles has been described as having a raw wound inside one's nervous system. Typically, affected individuals cannot even bear clothes touching the lesions. Even a light touch can produce a jolting reaction. Usually, the pain is greater in older patients.

The painful vesicles eventually become cloudy or darkened as they fill with blood, crust over within seven to ten days, and usually the crusts fall off and the skin heals. Sometimes, after severe blistering, scars and discolored skin remain.

Herpes zoster may have additional symptoms, depending on the dermatome involved. Herpes zoster ophthalmicus involves the orbit of the eye and occurs in approximately 10-25% of cases. Symptoms may include conjunctivitis, keratitis, uveitis, and optic nerve palsies that can sometimes cause chronic ocular inflammation, loss of vision, and debilitating pain. Herpes zoster oticus (i.e., Ramsay Hunt syndrome type II) involves the ear. Symptoms include hearing loss and vertigo.

The lesions and pain of shingles usually subside within three to five weeks, but about one in five patients (about one in two patients over age 70) suffer residual nerve pain for months or years, a condition called postherpetic neuralgia. This intensely painful condition is often difficult to manage. The pain may be a constant deep aching or burning. Brief bouts of burning sharp pain may also occur.

In some patients, shingles can reactivate presenting as zoster sine herpete. Pain radiates along the path of a single spinal nerve, but without an accompanying lesion. This condition may involve complications that affect several levels of the nervous system and cause multiple cranial neuropathies, polyneuritis, myelitis, or aseptic meningitis.

Shingles is more likely to occur in people whose immune system is impaired due to aging, immunosuppressive therapy, psychological stress, or other factors. A 2008 study revealed that people with close relatives who have had shingles are twice as likely to develop it themselves, thereby evidencing that genetic factors are involved in those who are more susceptible to VZV.

Current Prevention/Treatment

A live vaccine for VZV exists, marketed as Zostavax®. In a 2005 study of 38,000 older adults, it prevented half the cases of shingles and reduced the number of cases of postherpetic neuralgia by two-thirds. In October 2007, the vaccine was officially recommended in the U.S. for healthy adults aged 60 and over. However, it appears that as people age, the effectiveness of the vaccine diminishes. Additionally, since viruses mutate, the vaccine may lose its efficacy. Also, the vaccine is virtually useless after the onset of shingles. Moreover, numerous adverse reactions have reportedly been linked to the vaccine, ranging from causing a bout of shingles to allergic reactions and even death.

Once shingles is acquired, the aims of treatment are to shorten the duration of an episode, to limit the severity and duration of pain, and reduce complications. Symptomatic treatment is often needed for postherpetic neuralgia. Administration of the GABA analogue, gabapentin, has been found to offer some relief.

Antiviral drugs (e.g., acyclovir, valacyclovir, famciclovir) inhibit VZV replication and reduce the severity and duration of shingles. Antiviral treatment is recommended for all immunocompetent individuals over age 50 during the acute phase of shingles. However, it is critical that antiviral treatment is started within the therapeutic responsive window, i.e., within 72 hours of the first appearance of a characteristic lesion. After 72 hours, the efficacy of the antiviral treatment is greatly diminished.

In people who are at a high risk for repeated attacks of shingles (e.g., AIDS patients), antiviral drugs may be given prophylactically. However, since antiviral drugs may suppress the immune system, they may exacerbate pathological conditions of immunocompromised individuals. Additionally, antivirals are subject to drug resistance, as the pathogens mutate over time, becoming less susceptible to the treatment.

Typically, five daily oral doses of acyclovir are prescribed prophylactically. Common adverse drug reactions associated with systemic acyclovir therapy (oral or IV) include: nausea, vomiting, diarrhea and/or headache. Additional common adverse effects of IV acyclovir include encephalopathy, renal impairment, and injection site reactions.

The pain associated with shingles is treated with systemic analgesics. Occasionally, severe pain may require an opioid medication, such as morphine. Once the lesions have crusted over, capsaicin cream (Zostrix®) can be used. Topical lidocaine and nerve blocks may also reduce pain.

Accordingly, a need exists for an effective and safe method of preventing or inhibiting the pain associated with shingles and postherpetic neuralgia.

DETAILED DESCRIPTION OF THE INVENTION

The method of the present invention comprises the administration of a tetracycline compound to a human in an amount which is effective for the treatment of herpes zoster (shingles), but which has substantially no antibacterial activity. In the present invention, the treatment of shingles includes the prevention or attenuation of the pain associated with shingles.

In one embodiment, the tetracycline compound is administered prophylactically to an individual who is at risk of developing shingles. Individuals who are at risk of developing shingles include those who have had chicken pox, and who additionally have one or more of the following characteristics:
- are elderly (e.g., over age 65 years old);
- are under stress and/or are depressed;
- have a genetic predisposition to acquire shingles (e.g., individuals who have a close relative that has had shingles (e.g., members of a nuclear family));
- have weakened immune systems or are immunocompromised.

Individuals who have weakened immune systems include, for example, cancer patients, in particular those who are undergoing chemotherapy; individuals with transplants; individuals who take pharmaceuticals to suppress their immune response (e.g., corticosteroids, cyclosporine); individuals with HIV or AIDS; diabetics; individuals recovering from an illness, surgery or trauma; and individuals with poor nutrition.

Prophylactic administration of the tetracycline compound is especially suited for individuals who are at risk of developing shingles and cannot tolerate antiviral drugs for any reason. In fact, since antiviral drugs suppress the immune system, such drugs may be contraindicated for most individuals requiring a robust immune system to battle shingles. Prophylactic administration of the tetracycline compound is also especially suited for individuals who are at risk of developing shingles and cannot tolerate (or cannot benefit from) the VZV vaccine for any reason. For example, it is known that many elderly individuals do not react efficiently to vaccines.

Prophylactic administration of the tetracycline compound is administration before the onset of shingles. For example, administration is at least a few days before the onset of shingles, at least a week before the onset of shingles, at least two weeks before the onset of shingles, at least a month before the onset of shingles, at least six months before the onset of shingles, or at least a year before the onset of shingles.

In another embodiment, the tetracycline compound is administered as soon it is first suspected that the individual has shingles, preferably before lesions appear. The stage of shingles before lesions appear is typically termed "the prodromal stage." Such stage is about two days to about 2-3 weeks before the first lesion appears.

The earliest symptoms of the pre-lesion stage include feeling slightly unwell (e.g., headache, fever, nausea and/or malaise), and/or the development of a localized area of pain and tenderness. The localized area of pain and tenderness typically are only on one side of the body (i.e., left or right) not crossing the midline. The earliest symptoms are commonly followed by sensations such as, for example, burning pain, itching, hyperesthesia, paresthesia, stinging, aching, numbing, sensitivity to touch and/or throbbing in the localized area. Intermittent episodes of quick stabs of agonizing pain also can occur.

In another embodiment, treatment is begun at the first sign of a lesion associated with shingles. The shingles lesions start off as red spots, which quickly turn into blisters. They typically affect only one side of the body.

In another embodiment, a tetracycline compound is administered to inhibit the pain of postherpetic neuralgia.

In another embodiment, a tetracycline compound is administered to inhibit the pain of zoster sine herpete.

Tetracycline Compounds

The tetracycline compound can be an antibacterial or non-antibacterial compound. The tetracyclines are a class of compounds of which tetracycline is the parent compound. Tetracycline has the following general structure:

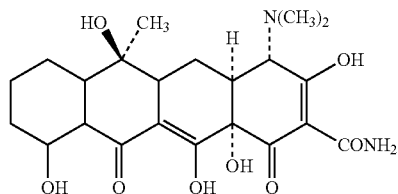 [SMILES: CN(C)[C@@H]1C(O)=C(C(N)=O)C(=O)[C@@]2(O)C(O)=C3C(=O)C4C(O)CCCC4[C@@](C)(O)C3C[C@@H]12]

The numbering system of the multiple ring nucleus is as follows:

Structure B

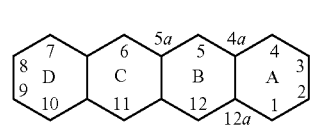

Tetracycline, as well as the 5-hydroxy(oxytetracycline, e.g., Terramycin) and 7-chloro (chlorotetracycline, e.g., Aureomycin) derivatives, exist in nature, and are all well known antibacterials. Semisynthetic derivatives such as 7-dimethylaminotetracycline (minocycline) and 6α-deoxy-5-hydroxytetracycline (doxycycline) are also known tetracycline antibacterials. Natural tetracyclines may be modified without losing their antibacterial properties, although certain elements of the structure must be retained to do so.

Some examples of antibacterial (i.e., antimicrobial) tetracycline compounds include doxycycline, minocycline, tetracycline, oxytetracycline, chlortetracycline, demeclocycline, lymecycline and their pharmaceutically acceptable salts.

Non-antibacterial tetracycline compounds are structurally related to the antibacterial tetracyclines, but have had their antibacterial activity substantially or completely eliminated by chemical modification. For example, non-antibacterial tetracycline compounds are at least about ten times, preferably at least about twenty five times, less antibacterial than doxycycline. In other words, non-antibacterial tetracycline compounds are incapable of achieving antibacterial activity comparable to that of doxycyline at concentrations at least about ten times, preferably at least about twenty five times, greater than that of doxycycline.

Examples of chemically modified non-antibacterial tetracyclines include 4-de(dimethylamino)tetracycline (COL-1), tetracyclinonitrile (COL-2), 6-demethyl-6-deoxy-4-de(dimethylamino)tetracycline (COL-3), 7-chloro-4-de(dimethylamino)-tetracycline (COL-4), tetracycline pyrazole (COL- 5), 4-hydroxy-4-de(dimethylamino)-tetracycline (COL-6), 4-de(dimethylamino-12α-deoxytetracycline (COL-7), 6-deoxy-5α-hydroxy-4-de(dimethylamino)tetracycline (COL-8), 4-de(dimethylamino)-12α-deoxyanhydrotetracycline (COL-9), and 4-de(dimethylamino)minocycline (COL-10).

Tetracycline derivatives, for purposes of the invention, may be any tetracycline derivative, including those compounds disclosed generically or specifically in U.S. Pat. No. 6,638,922, issued on Oct. 28, 2003 (assigned to Galderma Laboratories, L.P.), which are herein incorporated by reference. Examples include 9-amino-6-demethyl-6-deoxy-4-dedimethylaminotetracycline (COL-308) and 9-nitro-4-dedimethylaminominocycline (COL-1002).

Throughout this specification, parameters are defined by maximum and minimum amounts. Each minimum amount can be combined with each maximum amount to define a range.

According to the present invention, a tetracycline compound is administered in a sub-antibacterial amount. A sub-antibacterial amount of a tetracycline compound is any amount that results in a tetracycline plasma concentration: (i) which is effective to treat shingles, postherpetic neuralgia, and/or zoster sine herpete but (ii) which has no, or substantially no, antibacterial activity.

A treatment is effective if it causes one or more of: a reduction/inhibition/prevention of the pain/discomfort associated with shingles, especially, a reduction/inhibition/prevention of the pain/discomfort associated with shingles lesions; and/or shortening of the duration of an episode of shingles. A treatment is also effective if it reduces/inhibits/prevents postherpetic neuralgia, and/or zoster sine herpete; or if it reduces/inhibits/prevents the pain associated with postherpetic neuralgia, and/or zoster sine herpete.

A concentration of a tetracycline compound having substantially no antibacterial activity is any concentration that does not significantly prevent the growth of bacteria. That is, a microbiologist would not consider the growth of bacteria to be inhibited from a clinical point of view.

In one embodiment, the tetracycline compound is an antibacterial tetracycline compound. One way in which to quantify the antibacterial activities of tetracyclines is by a measure called minimum inhibitory concentration (MIC), as is known by a skilled artisan.

An MIC is the minimum tetracycline concentration that inhibits the growth of a particular strain of bacteria in vitro. MIC values are determined using standard procedures. Standard procedures are, for example, based on a dilution method (broth or agar), or an equivalent, using standard concentrations of inoculum and tetracycline powder. See, for example, National Committee for Clinical Laboratory Standards. *Performance Standards for Antimicrobial Susceptibility Testing—Eleventh Informational Supplement*. NCCLS Document M100-S11, Vol. 21, No. 1, NCCLS, Wayne, Pa., January, 2001.

In order to inhibit the growth of a strain of bacteria in vivo, a tetracycline compound achieves a plasma concentration in excess of the MIC for the strain. Plasma concentration refers to the concentration of a tetracycline compound measured in an individual's blood sample taken at steady state. Steady state is generally achieved after dosing for five to seven terminal half lives. The half lives of different tetracycline compounds vary from hours to days.

In the present invention, a tetracycline compound is administered in an amount that is effective, as described above, and that results in a plasma concentration which is significantly below the MIC for commonly-occurring bacteria. Such amounts are considered to have no, or substantially no, antibacterial activity. Examples of commonly-occurring bacteria that are susceptible to tetracyclines are *Escherichia coli* (e.g., ATCC 25922 and 25922); *Neisseria gonorrhoeae* (e.g., ATCC 49226); *Staphylococcus aureus* (e.g., ATCC 29213 and 25213); and *Streptococcus pneumoniae* (e.g., ATCC 49619).

For example, in the present invention, a tetracycline compound is administered in an amount that results in a plasma concentration which is less than approximately 80%, 75%, 70%, 65%, 60%, 55%, 50%, 45%, 40%, 35%, 30%, 25%, 20%, 15%, 10%, 5%, 1% or 0.5% of the MIC for the commonly-occurring bacteria mentioned above. A skilled artisan can readily determine the amount of a particular tetracycline compound to administer to achieve such concentrations.

For example, doxycycline is administered in an amount that results in a minimum steady state plasma concentration of about 0.1 μg/ml, 0.2 μg/ml, or 0.3 μg/ml, and a maximum steady state plasma concentration of about 0.7 μg/ml, 0.8 μg/ml, or 0.9 μg/ml.

The sub-antibacterial amount of an antibacterial tetracycline compound can also be expressed by daily dose. The daily dose of an antibacterial tetracycline compound is any amount that is sufficient to produce the effective, sub-antibacterial plasma concentrations described above. Such dose can, for example, be expressed as a percentage of a minimum antibacterial daily dose.

A skilled artisan knows, or is able routinely to determine, the minimum antibacterial daily dose for tetracycline compounds. Examples of suitable sub-antibacterial doses of antibacterial tetracycline compounds for the treatments described in the present specification include less than approximately: 80%, 75%, 70%, 65%, 60%, 55%, 50%, 45%, 40%, 35%, 30%, 25%, 20%, 15%, 10%, 5%, 1% and 0.5% of a minimum antibacterial dose.

Some examples of non-antibacterial daily doses of tetracycline compounds include about 20 mg/twice a day of doxycycline; about 38 mg of minocycline one, two, three or four times a day; and about 60 mg of tetracycline one, two, three or four times a day.

There is no necessary minimum effective amount of the tetracycline compound, as long as the amount administered is capable of providing the effective treatment. For example, when the amount is expressed as a percentage of the MIC plasma concentration, suitable minimum plasma concentrations include approximately 0.1%, 0.5%, 0.8% and 1% of the MIC plasma concentration. When the amount is expressed as a minimum actual plasma concentration, suitable actual plasma concentrations include approximately 0.01 μg/ml, 0.05 μg/ml, 0.1 μg/ml, 0.15 μg/ml, 0.2 μg/ml, 0.25 μg/ml and 0.3 μg/ml. When the dose is expressed as a percentage of a minimum antibacterial daily dose, the percentage is approximately 0.1%, 0.2%, 0.5%, 1%, 1.5% and 2% of the minimum antibacterial dose.

In a preferred embodiment, any form of doxycycline (e.g., doxycycline salts, such as doxycycline hyclate; and doxycycline hydrates, such as doxycycline monohydrate) is administered in a daily amount of, or equivalent to, from about 10 to about 60 milligrams of doxycycline, while maintaining a concentration in human plasma below the MIC.

In an especially preferred embodiment, doxycycline, a doxycycline salt, or a doxycycline hydrate, is administered at a dose of, or equivalent to, 20 milligrams of doxycycline twice daily. Such a formulation is sold for the treatment of periodontal disease under the trademark Periostat®.

The below Example summarizes an incidence using 20 mg doxycycline hyclate tablets administered twice a day. A virtually complete inhibition of the pain typically associated with lesions of shingles was observed.

In another embodiment, the tetracycline compound is a non-antibacterial tetracycline compound, such as the COLs discussed above. Since COLs have no, or substantially no, antibacterial activity, they can be administered at any effective dose at which side effects, if any, are acceptable. There is no risk of indiscriminate killing of bacteria, and the resulting threat of developing resistant bacteria.

For example, suitable maximum plasma concentrations of the COLs mentioned above include up to about 100 µg/ml, about 200 µg/ml and about 300 µg/ml. Suitable maximum daily doses of COLs include about 18 mg/kg/day, about 40 mg/kg/day, about 60 mg/kg/day and about 80 mg/kg/day.

An example of a COL is 6-demethyl-6-deoxy-4-de(dimethylamino)tetracycline (COL-3). COL-3 is administered in doses of up to about 200 mg/day, preferably about 150 mg/day, more preferably about 100 mg/day, or in amounts that result in plasma concentrations of up to about 50 µg/ml, about 40 µg/ml or about 30 µg/ml. For example, a dose of about 10 to about 20 mg/day of COL-3 produces plasma concentrations in humans of about 1.0 µg/ml.

There is no necessary minimum effective dose of COLs. Some typical minimum plasma concentrations of COLs include, for example, about 0.01 µg/ml, 0.1 µg/ml, 0.8 µg/ml, and 1.0 µg/ml. Some typical minimum daily doses of COLs include about 0.05 mg/day, about 0.1 mg/day, about 0.5 mg/day, about 1 mg/day, about 5 mg/day, or about 10 mg/day.

In a preferred embodiment, any of the doses of any of the tetracycline compounds mentioned above, e.g., doxycycline and COL-308, are administered by controlled release over a 24 hour period. For example, doxycycline is preferably administered in an amount of about 40 milligrams over the 24 hour period.

In another embodiment, the tetracycline compound is administered as a pharmaceutical composition comprising an active ingredient wherein the active ingredient consists essentially of a tetracycline compound in an amount that is effective to treat the conditions described in the present specification, but has substantially no antibacterial activity.

The actual preferred amounts of tetracycline compounds in a specified case will vary according to the particular compositions formulated, the mode of application, the particular sites of application, and the subject being treated (e.g., age, gender, size, tolerance to drug, etc.)

The tetracycline compounds can be in the form of pharmaceutically acceptable salts of the compounds. The term "pharmaceutically acceptable salt" refers to a salt prepared from a well-tolerated, nontoxic tetracycline compound and an acid or base. The acids may be inorganic or organic acids of tetracycline compounds. Examples of inorganic acids include hydrochloric, hydrobromic, nitric hydroiodic, sulfuric, and phosphoric acids. Examples of organic acids include carboxylic and sulfonic acids. The radical of the organic acids may be aliphatic or aromatic. Some examples of organic acids include formic, acetic, phenylacetic, propionic, succinic, glycolic, glucuronic, maleic, furoic, glutamic, benzoic, anthranilic, salicylic, phenylacetic, mandelic, embonic (pamoic), methanesulfonic, ethanesulfonic, panthenoic, benzenesulfonic, stearic, sulfanilic, alginic, tartaric, citric, gluconic, gulonic, arylsulfonic, and galacturonic acids. Appropriate organic bases may be selected, for example, from N,N-dibenzylethylene-diamine, chloroprocaine, choline, diethanolamine, ethylenediamine, meglumine (N-methylglucamine), and procaine.

The tetracycline compounds of the invention can be administered without administering a bisphosphonate compound. Bisphosphonates compounds are related to inorganic pyrophosphonic acid. The bisphosphonates include, as non-limiting examples, alendronate (4-amino-1-hydroxybutylidene bisphosphonic acid), clodronate (dichloromethane diphosphonic acid), etidronate (1-hydroxyethylidene diphosphanic acid) and pamidronate (3-amino-1-hydroxypropylidene bisphosphonic acid); also risedronate ([2-(3-pyridinyl)ethylidene]hydroxy bisphosphonic acid), tiludronate, i.e., tiludronic acid (4-chlorophenylthiomethylene bisphosphonic acid) and zolendronate.

Preferably, the tetracycline compounds have low phototoxicity, or are administered in an amount that results in a plasma level at which the phototoxicity is acceptable. Phototoxicity is a chemically-induced photosensitivity. Such photosensitivity renders skin susceptible to damage, e.g., sunburn, blisters, accelerated aging, erythemas and eczematoid lesions, upon exposure to light, in particular ultraviolet light. The preferred amount of the tetracycline compound produces no more phototoxicity than is produced by the administration of a 40 mg total daily dose of doxycycline.

Examples of tetracycline compounds with low phototoxicity include, but are not limited to, tetracycline compounds having general formulae:

Structure K

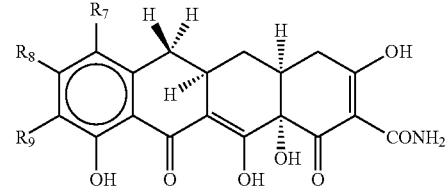

wherein: R7, R8, and R9 taken together in each case, have the following meanings:

| R7 | R8 | R9 | |
|---|---|---|---|
| hydrogen | hydrogen | amino | (COL-308) |
| hydrogen | hydrogen | palmitamide | (COL-311) |
| hydrogen | hydrogen | dimethylamino | (COL-306) | and

Structure L

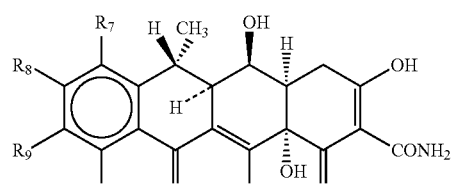

Structure M

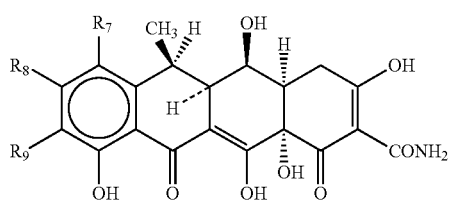

-continued

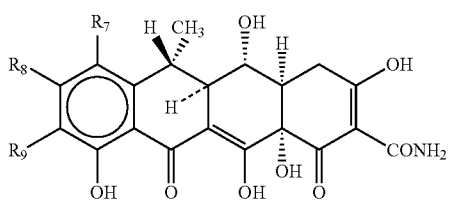

Structure N

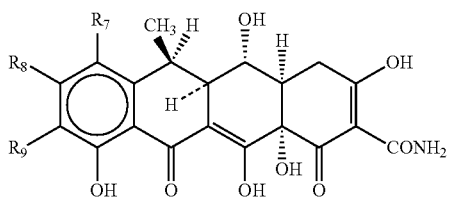

Structure O wherein: R7, R8, and R9 taken together in each case, have the following meanings:

| R7 | R8 | R9 | |
|---|---|---|---|
| hydrogen | hydrogen | acetamido | (COL-801) |
| hydrogen | hydrogen | dimethylaminoacetamido | (COL-802) |
| hydrogen | hydrogen | palmitamide | (COL-803) |
| hydrogen | hydrogen | nitro | (COL-804) |
| hydrogen | hydrogen | amino | (COL-805) | and

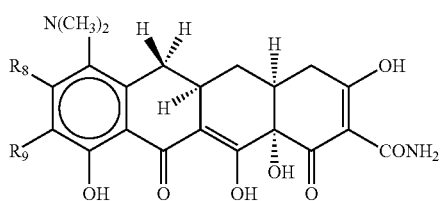

Structure P wherein: R8, and R9 taken together are, respectively, hydrogen and nitro (COL-1002).

The tetracycline compounds may be administered by methods known in the art. For example, the tetracycline compounds may be administered systemically. For the purposes of this specification, "systemic administration" means administration to a human by a method that causes the compounds to be absorbed into the bloodstream.

Preferably, the tetracycline compounds are administered orally by any method known in the art. For example, tetracyclines can be administered in the form of tablets, capsules, pills, troches, elixirs, suspensions, syrups, wafers, chewing gum and the like.

Additionally, the tetracycline compounds can be administered enterally or parenterally, e.g., intravenously; intramuscularly; subcutaneously, as injectable solutions or suspensions; intraperitoneally; or rectally. Administration can also be intranasally, in the form of, for example, an intranasal spray; or transdermally, in the form of, for example, a patch.

For the pharmaceutical purposes described above, the tetracycline compounds of the invention can be formulated per se in pharmaceutical preparations, optionally, with a suitable pharmaceutical carrier (vehicle) or excipient, as understood by practitioners in the art. These preparations can be made according to conventional chemical methods.

In the case of tablets for oral use, carriers commonly used include lactose and corn starch, and lubricating agents such as magnesium stearate are commonly added. For oral administration in capsule form, useful carriers include lactose and corn starch. Further examples of carriers and excipients include milk, sugar, certain types of clay, gelatin, stearic acid or salts thereof, calcium stearate, talc, vegetable fats or oils, gums and glycols.

When aqueous suspensions are used for oral administration, emulsifying and/or suspending agents are commonly added. In addition, sweetening and/or flavoring agents may be added to the oral compositions.

For intramuscular, intraperitoneal, subcutaneous and intravenous use, sterile solutions of the tetracycline compounds can be employed, and the pH of the solutions can be suitably adjusted and buffered. For intravenous use, the total concentration of the solute(s) can be controlled in order to render the preparation isotonic.

The tetracycline compounds of the present invention can further comprise one or more pharmaceutically acceptable additional ingredient(s) such as alum, stabilizers, buffers, coloring agents, flavoring agents, and the like.

The tetracycline compounds may be administered at intervals. For example, the tetracycline compound may be administered 1-6 times a day, preferably 1-4 times a day.

The tetracycline compounds may be administered by controlled release. Controlled release administration is a method of drug delivery to achieve a certain level of the drug over a particular period of time. The level typically is measured by plasma concentration. Methods for controlled release of drugs are well known in the art. Further description of methods of delivering tetracycline compounds by controlled release can be found in international patent application PCT/US02/10748 (assigned to Galderma Laboratories, L.P.) which is incorporated herein by reference in its entirety.

In another embodiment, non-antibacterial tetracycline compounds can be administered topically to the painful skin areas associated with shingles, in particular on painful lesions, (or administered topically to the affected skin areas of postherpetic neuralgia or zoster sine herpete). Particular non-antibacterial tetracycline compounds have only limited biodistribution, e.g., COL-5. In such cases, topical application is the preferred method of administration of the compound.

Carrier compositions deemed to be suited for topical use include gels, salves, lotions, creams, ointments, and the like. The non-antibacterial tetracycline compounds can also be incorporated into a support base, matrix, tissue adhesive, or the like which can be directly applied to the oral mucosa.

Topical application of the non-antibacterial tetracycline compounds is effective while not inducing significant toxicity in the human. For example, amounts of up to about 25% (w/w) in a vehicle are effective. Amounts of from about 0.1% to about 10% are preferred.

Combined or coordinated topical and systemic administration of the tetracycline compounds is also contemplated under the invention. For example, a non-absorbable non-antibacterial tetracycline compound can be administered topically, while a tetracycline compound capable of substantial absorption and effective systemic distribution in a human can be administered systemically.

The tetracycline compounds are prepared by methods known in the art. For example, natural tetracyclines may be modified without losing their antibacterial properties, although certain elements of the structure must be retained. The modifications that may and may not be made to the basic tetracycline structure have been reviewed by Mitscher in *The Chemistry of Tetracyclines*, Chapter 6, Marcel Dekker, Publishers, New York (1978). According to Mitscher, the substituents at positions 5-9 of the tetracycline ring system may be modified without the complete loss of antibacterial properties. Changes to the basic ring system or replacement of the substituents at positions 1-4 and 10-12, however, generally lead to synthetic tetracyclines with substantially less or effectively no antibacterial activity.

In some embodiments, along with a tetracycline compound, Vitamin $B_{12}$ is administered in about 250 to about 1000 mcg daily dose, or in about 400 to about 700 mcg daily dose, or in about 500 to about 625 mcg daily dose. Vitamin $B_{12}$ enhances the effect of the tetracycline compound.

In some embodiments, along with a tetracycline compound, a vitamin B complex is administered. The vitamin B complex can include one or all of the following: Vitamin $B_{12}$ in about 250 to about 1000 mcg daily dose, and/or Vitamin $B_1$, Vitamin $B_2$, niacin and/or Vitamin $B_6$ all in about 100 to about 200 mg daily dose, and/or folic acid in about 300 to about 500 mcg daily dose, and/or biotin in about 100 to about 200 mcg daily dose, pantothenic acid, inositol, and/or para-aminobenzoic acid all in about 100 to about 200 mg daily dose and/or choline in about 50 to about 70 mg daily dose.

In some embodiments, a selective serotonergic reuptake inhibitor is administered along with the tetracycline compound. For example, citalopram in about a 10 mg to about a 20 mg daily dose is administered.

Preferably, the human is monitored during treatment. Monitoring is accomplished by observing a positive treatment result. After a positive result is observed, treatment is continued.

EXAMPLE

The following example serves to provide further appreciation of the invention but is not meant in any way to restrict the effective scope of the invention.

An 84 year old man (hereinafter "the patient") had been taking generic Periostat® (20 mg doxycycline hyclate b.i.d.) for over a six month period when he presented with shingles. The patient did not seek medical attention for his shingles until over 96 hours after the appearance of his first lesion. By this time, the patient had blistering and vesicular lesions, and lesions consisting of deep scabs on his face (e.g., upper cheek), neck and chest. All lesions presented on patient's left side without crossing the midline.

The patient also reported being lethargic, weak and dizzy. The patient did not report any pain.

The medical doctor who examined the patient was very surprised to hear that the lesions were not painful. She said that the lesions were at the stage where they typically cause intense pain. The doctor predicted that, even if the lesions were not painful at the moment, they would become very painful shortly, particularly since antiviral therapy would be initiated after 72 hours of the appearance of the characteristic lesions. Accordingly, the doctor prescribed the narcotic pain reliever Percocet®.

The doctor also prescribed VALTREX®, an antiherpetic medication, in a dose of a 1 gram tablet, taken 3 times a day for 7 days. The doctor advised that VALTREX® should have been started within 2 or 3 days of the first appearance of a lesion in order to effectively minimize pain.

The patient began taking the VALTREX®, as prescribed. However, the patient did not fill the prescription for the narcotic pain reliever, and did not take any other analgesic.

Throughout the course of his shingles, the patient stated that he did not feel any pain whatsoever. The only sensation (associated with the lesions) reported by the patient was that "he knew that the lesions were present since they rubbed against his clothes." The patient continued to feel lethargic and weak for a couple of weeks. As of about nine weeks after the presentation of the first lesion, discolorations remain on the areas of the patient's skin where the lesions were present.

Chemical Names of the Col Compounds

| | |
|---|---|
| COL-1 | 4-dedimethylaminotetracycline |
| COL-3 | 6-demethyl-6-deoxy-4-dedimethylaminotetracycline |
| COL-301 | 7-bromo-6-demethyl-6-deoxy-4-dedimethylaminotetracycline |
| COL-302 | 7-nitro-6-demethyl-6-deoxy-4-dedimethylaminotetracycline |
| COL-303 | 9-nitro-6-demethyl-6-deoxy-4-dedimethylaminotetracycline |
| COL-304 | 7-acetamido-6-demethyl-6-deoxy-4-dedimethylaminotetracycline |
| COL-305 | 9-acetamido-6-demethyl-6-deoxy-4-dedimethylaminotetracycline |
| COL-306 | 9-dimethylamino-6-demethyl-6-deoxy-4-dedimethylaminotetracycline |
| COL-307 | 7-amino-6-demethyl-6-deoxy-4-dedimethylaminotetracycline |
| COL-308 | 9-amino-6-demethyl-6-deoxy-4-dedimethylaminotetracycline |
| COL-309 | 9-dimethylaminoacetamido-6-demethyl-6-deoxy-4-dedimethylaminotetracycline |
| COL-310 | 7-dimethylamino-6-demethyl-6-deoxy-4-dedimethylaminotetracycline |
| COL-311 | 9-palmitamide-6-demethyl-6-deoxy-4-dedimethylaminotetracycline |
| COL-312 | 2-CONHCH$_2$-pyrrolidin-1-yl-6-demethyl-6-deoxy-4-dedimethylaminotetracycline |
| COL-313 | 2-CONHCH$_2$-piperidin-l-yl-6-demethyl-6-deoxy-4-dedimethylaminotetracycline |
| COL-314 | 2-CONHCH$_2$-morpholin-1-yl-6-demethyl-6-deoxy-4-dedimethylaminotetracycline |
| COL-315 | 2-CONHCH$_2$-piperazin-1-yl-6-demethyl-6-deoxy-4-dedimethylaminotetracycline |
| COL-4 | 7-chloro-4-dedimethylaminotetracycline |
| COL-5 | tetracycline pyrazole |
| COL-6 | 4-hydroxy-4-dedimethylaminotetracycline |
| COL-7 | 4-dedimethylamino-12α-deoxytetracycline |
| COL-8 | 4-dedimethylaminodoxycycline |
| COL-801 | 9-acetamido-4-dedimethylaminodoxycycline |
| COL-802 | 9-dimethylaminoacetamido-4-dedimethylaminodoxycycline |
| COL-803 | 9-palmitamide-4-dedimethylaminodoxycycline |
| COL-804 | 9-nitro-4-dedimethylaminodoxycycline |
| COL-805 | 9-amino-4-dedimethylaminodoxycycline |
| COL-806 | 9-dimethylamino-4-dedimethylaminodoxycycline |
| COL-807 | 2-CONHCH$_2$-pyrrolidin-1-yl-4-dedimethylaminodoxycycline |
| COL-808 | 2-CONHCH$_2$-piperidin-1-yl-4-dedimethylaminodoxycycline |
| COL-809 | 2-CONHCH$_2$-piperazin-1-yl-4-dedimethylaminodoxycycline |
| COL-10 | 4-dedimethylaminominocycline (a.k.a. COL-310) |
| COL-1001 | 7-trimethylammonium-4-dedimethylaminosancycline |
| COL-1002 | 9-nitro-4-dedimethylaminominocycline |

The invention claimed is:

1. A method of treating shingles in a human in need thereof, the method comprising administering systemically to the human an antibacterial tetracycline compound, or a pharmaceutically acceptable salt thereof, in an amount that is effective to treat shingles but has substantially no antibacterial activity,
    wherein the antibacterial tetracycline compound is doxycycline administered in a daily amount of from 10 to 60 milligrams.

2. A method according to claim 1, wherein treatment is begun before the onset of shingles, after the onset of shingles but before the appearance of a lesion, or at the appearance of a lesion.

3. A method according to claim 1, wherein the antibacterial tetracycline compound, or a pharmaceutically acceptable salt thereof, is administered in an amount that results in a plasma concentration which is less than approximately 80%, 75%, 70%, 65%, 60%, 55%, 50%, 45%, 40%, 35%, 30%, 25%, 20%, 15%, 10%, 5%, 1% or 0.5% of MIC of the tetracycline compound for commonly-occurring bacteria.

4. A method according to claim 1, wherein the antibacterial tetracycline compound, or a pharmaceutically acceptable salt thereof, is administered in an amount which is less than approximately 80%, 75%, 70%, 65%, 60%, 55%, 50%, 45%, 40%, 35%, 30%, 25%, 20%, 15%, 10%, 5%, 1% or 0.5% of the minimum antibacterial dose.

5. A method according to claim 1, wherein the doxycycline, or a pharmaceutically acceptable salt thereof, is administered twice a day in a dose of about 20 mg.

6. A method according to claim 1, wherein the doxycycline, or a pharmaceutically acceptable salt thereof, is administered by controlled release over a 24 hour period.

7. A method according to claim 6, wherein the doxycycline, or a pharmaceutically acceptable salt thereof, is administered in an amount of about 40 milligrams.

8. A method according to claim 1, wherein the doxycycline, or pharmaceutically acceptable salt thereof, is administered in an amount which results in a plasma concentration in the range of about 0.1 to about 0.8 µg/ml.

9. A method according to claim 1, wherein the systemic administration is oral administration or intravenous injection.

10. A method of treating shingles in a human in need thereof, the method comprising administering systemically to the human an antibacterial tetracycline compound, or a pharmaceutically acceptable salt thereof, in an amount that is effective to treat shingles but has substantially no antibacterial activity, wherein the tetracycline compound is minocycline administered at 38 mg one, two, three or four times a day, or wherein the tetracycline compound is tetracycline administered at 60 mg one, two, three or four times a day.

11. A method according to claim 10, wherein treatment is begun before the onset of shingles, after the onset of shingles but before the appearance of a lesion, or at the appearance of a lesion.

12. A method according to claim 10, wherein the antibacterial tetracycline compound, or pharmaceutically acceptable salt thereof, is administered in an amount that results in a plasma concentration which is less than approximately 80%, 75%, 70%, 65%, 60%, 55%, 50%, 45%, 40%, 35%, 30%, 25%, 20%, 15%, 10%, 5%, 1% or 0.5% of MIC of the tetracycline compound for commonly-occurring bacteria.

13. A method according to claim 10, wherein the antibacterial tetracycline compound, or pharmaceutically acceptable salt thereof, is administered in an amount which is less than approximately 80%, 75%, 70%, 65%, 60%, 55%, 50%, 45%, 40%, 35%, 30%, 25%, 20%, 15%, 10%, 5%, 1% or 0.5% of the minimum antibacterial dose.

14. A method according to claim 10, wherein the antibacterial tetracycline, or pharmaceutically acceptable salt thereof, is administered in an amount which results in a plasma concentration in the range of about 0.1 to about 0.8 µg/ml.

15. A method according to claim 10, wherein the systemic administration is oral administration or intravenous injection.

* * * * *